United States Patent
Davey et al.

[11] Patent Number: 6,025,489
[45] Date of Patent: Feb. 15, 2000

[54] TRICYCLIC PTERIDINONES AND A PROCESS FOR THEIR PREPARATION

[75] Inventors: David D. Davey, El Sobrante, Calif.; John W. Lampe, Apex, N.C.

[73] Assignee: Schering Aktiengesellschaft, Berlin, Germany

[21] Appl. No.: 09/216,552

[22] Filed: Dec. 18, 1998

Related U.S. Application Data

[63] Continuation-in-part of application No. 07/961,987, Oct. 16, 1992, Pat. No. 5,854,419, which is a continuation-in-part of application No. 07/844,324, Mar. 2, 1992, abandoned, which is a continuation of application No. 07/649,384, Feb. 1, 1991, abandoned, which is a continuation-in-part of application No. 07/437,574, Nov. 17, 1989, abandoned.

[30] Foreign Application Priority Data

Nov. 12, 1990 [EP] European Pat. Off. .............. 0 429 149

[51] Int. Cl.[7] .................................................. C07D 417/00
[52] U.S. Cl. ............................ 544/60; 544/115; 544/251; 544/322
[58] Field of Search .............................. 544/60, 115, 251, 544/322

[56] References Cited

U.S. PATENT DOCUMENTS

| | | | |
|---|---|---|---|
| 4,229,452 | 10/1980 | Warner, Jr. et al. | 424/250 |
| 4,440,929 | 4/1984 | Lee et al. | 544/346 |
| 4,446,323 | 5/1984 | Freed et al. | 544/344 |
| 4,696,928 | 9/1987 | Ellames et al. | 514/250 |
| 4,904,658 | 2/1990 | Tseng et al. | 514/233.2 |
| 5,602,252 | 2/1997 | Davey | 544/115 |

FOREIGN PATENT DOCUMENTS 2106109  4/1983  United Kingdom .

OTHER PUBLICATIONS

Brown, D. J. et al., Triazolopteridines II* Simple s–Triazolo [3,4–h]pteridines and Some [5,1–h] and [4,3–a] Isomers, *Aust. J. Chem.* (1981) 34:2635–9.

Parthasarathy, P.C. et al., Heterocyclic N–Oxides: Part II–Syntheses of New Ring Systems N–Oxides of Dihydroimidazo & Pyrimido [2,1–h]pteridines & Azadihydroimidazo & Pyrimido[1,2–a]quinoxalines & Their Antiprotozoal Activities, *Indian Journal of Chemistry*, (1983) 22B:1233–1235.

Gakhar, H.K. et al., Substituted Benzimidazo[2,1–h]pteridine–2,4–diones, *Monatshefte für Chemie* (1984) 115:757–763.

Oguchi, et. al., "Syntheses of Quinoxaline . . . ", Chem. Abs., vol. 96 (1982), Abs.# 162646z, pp. 751–752.

Sakamoto et. al., "Preparation of Imidazoquinoxalinones . . . ", Chem. Abs., vol. 120 (1994), Abs.# 217730u, pp. 1088–1089.

*Primary Examiner*—Mukund J. Shah
*Assistant Examiner*—Tamthom N. Truong
*Attorney, Agent, or Firm*—Carol J. Roth

[57] ABSTRACT

This invention is directed to tricyclic pteridinones of formula (I):

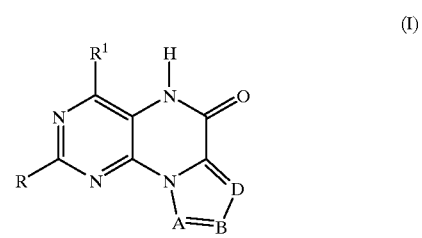

where R, $R^1$, A, B and D are described herein. These compounds and their pharmaceutically acceptable salts are disclosed as being combined inotropic and vasodilator agents.

6 Claims, No Drawings

TRICYCLIC PTERIDINONES AND A PROCESS FOR THEIR PREPARATION

This application is a continuation-in-part of U.S. patent application Ser. No. 07/961,987, filed Oct. 16, 1992, now U.S. Pat. No. 5,854,419, which is a continuation-in-part application of U.S. patent application Ser. No. 07/844,324, filed Mar. 2, 1992, now abandoned, which is a continuation of U.S. patent application Ser. No. 07/649,384, filed Feb. 1, 1991, now abandoned, which is a continuation-in-part of U.S. patent application Ser. No. 07/437,574, filed Nov. 17, 1989, now abandoned. The disclosure of these applications are incorporated herein in full by reference.

FIELD OF INVENTION

This invention relates to novel tricyclic pteridinones, their aza analogs and their pharmaceutically acceptable salts. Further encompassed by the invention is a novel process for the production of the tricyclic pteridinones and their aza analogs. The compounds of the invention exhibit a variety of pharmacological properties for which pharmaceutical compositions are proposed.

General Description of the Invention Composition-of-Matter Aspect

In its composition-of-matter aspect, this invention relates to novel tricyclic pteridinones, their aza analogs and the pharmaceutically acceptable salts thereof.

Compounds encompassed by the invention are of the following formula (I):

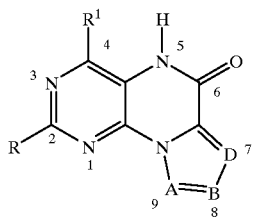

(I)

wherein

A is N or $C(R^2)$;

B is N or $C(R^2)$;

D is N or $C(R^3)$;

R is hydrogen, hydroxy, loweralkyl, loweralkoxy, cycloalkyl, aryl, aryloxy, pyridinyl, 3-pyridinyloxy, $R^6S(O)_n$, W—ALK—Q, or —N$(R^7)_2$;

or R is

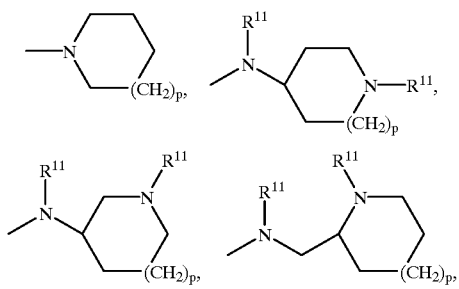

-continued

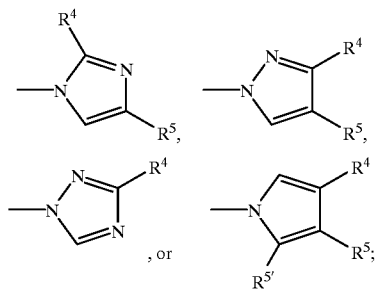

$R^1$ is hydrogen, hydroxy, loweralkyl, loweralkoxy, cycloalkyl, aryl, aryloxy, pyridinyl, 3-pyridinyloxy, $R^6S(O)_n$, W—ALK—Q, or —N$(R^7)_2$, or $R^1$ is

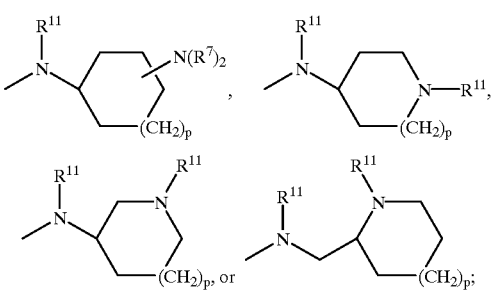

$R^2$ is hydrogen, $C_1$–$C_8$ straight or branched chain alkyl optionally substituted by 2 adjacent hydroxyl groups, $C_3$–$C_8$ straight or branched chain alkenyl, loweralkylloweralkoxy, aryl, pyridinyl, loweralkylcycloalkyl, loweralkylaryl, loweralkylpyridinyl, loweralkylaryloxy, loweralkylpyridinyloxy, loweralkyl-N$(R^6)_2$, or

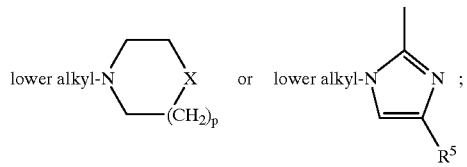

$R^3$ is hydrogen, loweralkyl, aryl, pyridinyl, loweralkylaryloxy, or loweralkylpyridinyl;

$R^4$ is hydrogen, $C_1$–$C_8$ straight or branched chain alkyl, $C_3$–$C_8$ straight or branched chain alkenyl, loweralkylcycloalkyl or loweralkylaryl;

$R^5$ and $R^{5'}$ are the same or independently hydrogen or loweralkyl;

$R^6$ is loweralkyl, aryl, pyridinyl, loweralkylaryl or loweralkylpyridinyl; each $R^7$ is the same or independently hydrogen, loweralkyl, aryl or pyridinyl;

$R^8$ is the same as $R^7$;

Q is —O—, —N$(R^9)$—, —S—, —CH$_2$O—, —CH$_2$N$(R^9)$— or —CH$_2$S—;

W is hydrogen, hydroxy, loweralkyl, loweralkoxy, aryl, aryloxy, pyridinyl which may be substituted by one or two hydroxy groups, pyridinyloxy, —N$(R^{10})_2$, or

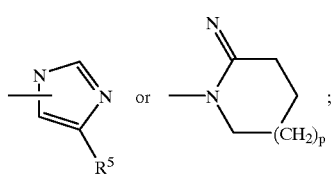

$R^9$ and $R^{10}$ have the same meaning as $R^7$;

$R^{11}$ are the same or independently hydrogen or methyl;

X is —$CH_2$—, —O—, —$S(O)_n$—, —$NR^{10}$—;

ALK is a $C_1$–$C_4$ straight or branched chain alkyl optionally substituted by a mono hydroxyl group which cannot be attached to the carbon atom adjacent to Q or W when Q or W are heteroatoms, and n is 0, 1 or 2; and p is 0 or 1, or a pharmaceutically acceptable salt thereof.

Inclusive of the compounds of formula (I) are the provisos that:

(a) only one of A and B is N; and (b) only one of B and D is N.

As used herein, the term "lower" when used conjunctively with alkyl, alkoxy, cycloalkyl or aryl shall represent a straight or branched chain alkyl of one to four carbon atoms as for example methyl, ethyl, propyl, isopropyl, butyl, sec-butyl, isobutyl and tertiary butyl. The term $C_1$–$C_4$ straight or branched chain alkyl will include the same entities. The term $C_1$–$C_8$ straight or branched alkyl shall be inclusive of the above terms, plus, for example, n-pentyl, isopentyl, β-methylbutyl, γ-methylbutyl, β,β-dimethylpropyl, n-hexyl, δ-methylpentyl, β-ethylbutyl, γ-ethylbutyl, n-heptyl, isoheptyl, ε-methylheptyl, β-ethylpentyl, γ-ethylpentyl, δ-ethylpentyl, γ-propylbutyl, n-octyl, β-ethylhexyl, δ-ethylhexyl, β-ethylhexyl, β-propylpentyl, γ-propylpentyl. $C_3$–$C_8$ straight or branched chain alkenyl shall include, for example, α-propenyl, β-propenyl, isopropenyl, β-methylpropenyl, α-butenyl, β-butenyl, δ-butenyl, β-methyl-β-butenyl, and β-ethyl-β-hexenyl. Cycloalkyl shall be taken to mean a saturated carbocycle of from three to five carbon atoms such as cyclopropyl, cyclobutyl, cyclopentyl, cyclohexyl, cycloheptyl, or cyclooctyl. The term aryl shall be taken to mean a phenyl group optionally substituted with from one to 3 moieties selected from hydroxy, methoxy or chlorine.

Contemplated as part of this invention are the pharmaceutically acceptable salts of the compounds of formula (I). These may be acid or base addition in nature. The acid addition salts may be formed with inorganic or organic acids. Illustrative but not restrictive examples of such acids include hydrochloric, hydrobromic, sulfuric, phosphoric, citric, acetic, propionic, benzoic, naphthoic, oxalic, succinic, maleic, malic, adipic, lactic, tartaric, salicylic, methanesulfonic, 2-hydroxyethanesulfonic, toluenesulfonic, benzenesulfonic, camphorsulfonic and ethanesulfonic acids. The base addition salts may be formed with the metal ions as for example, sodium, potassium or calcium.

It is understood that the definition of the compounds of formula (I) encompasses all possible stereoisomers and mixtures thereof, which possess the activities discussed below. In particular, it encompasses the geometric and optical isomers and the racemic modifications thereof which possess the indicated activity.

It is also understood that the definition of the compounds of formula (I) encompasses all polymorphic modifications and other solid state modifications which possess the stated activity.

The compounds which follow are some of those which serve to exemplify various aspects of the invention described herein.

1. 9-butyl-4-ethyl-2-(1H-imidazol-1-yl)imidazo[5,1-h]pteridin-6(5H)-one.

2. 4,9-diethyl-7-methyl-2-methylthioimidazo[5,1-h]pteridin-6(5H)-one.

3. 4,9-diethyl-7-methyl-2-methylsulfonylimidazo[5,1-h]pteridin-6(5H)-one.

4. 4,9-diethyl-2-[(2-diethylaminoethyl)amino]-7-methylimidazo[5,1-h]pteridin-6(5H)-one.

5. 2-amino-4,9-diethyl-7-methylimidazo[5,1-h]pteridin-6(5H)-one.

6. 4-ethyl-2-(1H-imidazol-1-yl)-9-(2-phenylethyl)imidazo[5,1-h]pteridin-6(5H)-one.

7. 2-[[(3,4-dimethoxyphenyl)methyl]amino]-4,9-diethyl-7-methylimidazo[5,1-h]pteridin-6(5H)-one.

8. 4,9-diethyl-7-methyl-2-[(phenylmethyl)amino]imidazo[5,1-h]pteridin-6(5H)-one.

9. 4,9-diethyl-2-[3-(1H-imidazol-1-yl)propylamino]-7-methylimidazo[5,1-h]pteridin-6(5H)-one.

10. 8,9-diethyl-4-[(1-methyl-4-piperidinyl)amino]imidazo[5,1-h]pteridin-6(5H)-one.

As stated previously, the compounds of the invention have been found to exhibit a variety of pharmacologic effects. More particularly, the compounds exhibit vasodilator effects with little or no inotropic activity, thus the compounds would be useful in the selective vascular treatment of congestive heart failure, angina, hypertension and broncho congestion. Some of the compounds have also been found to have antiarrhythmic effects. Sub genera to the general compounds of formula (I) certain groups of compounds have been found to have potent PDE inhibiting and cGMP potentiating effects. These are:

(a) where $R^1$ is loweralkyl and B or D is N;

(b) where $R^1$ is a nitrogen connection and B is N; or (c) where $R^1$ is a diamine grouping and B or D is N.

Process Aspect

The novel tricyclic pteridinones and their aza analogs, the subject of this invention, are prepared essentially as illustrated in the following Schemes A, A/2, B and C, which Schemes are inclusive of a novel cyclization step.

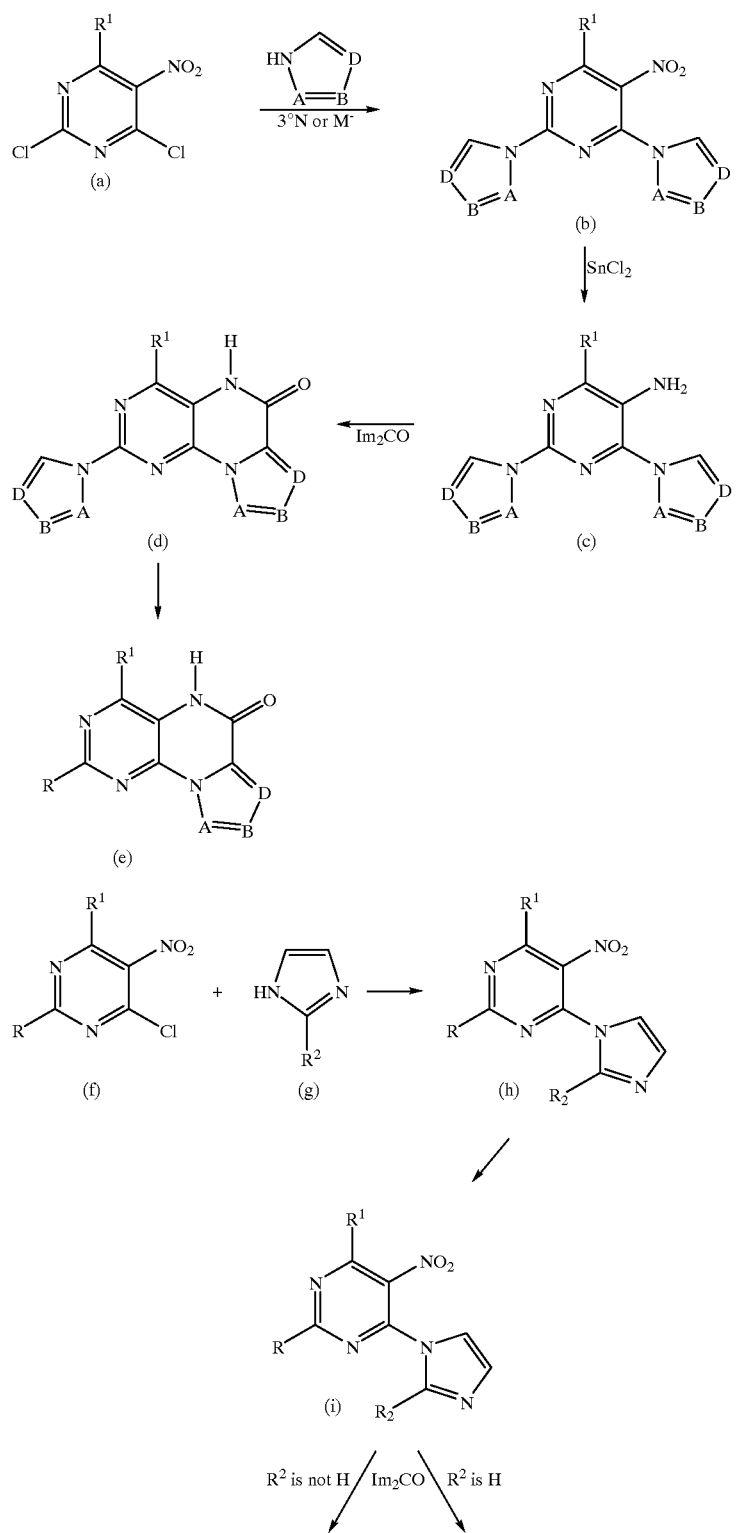

-continued
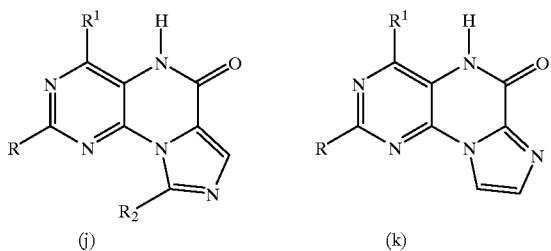
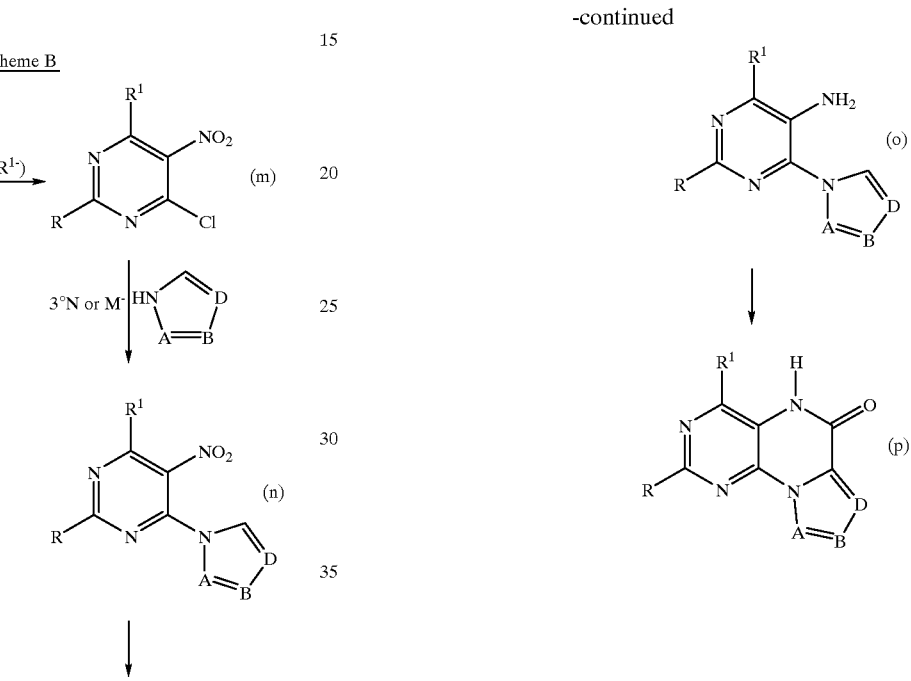
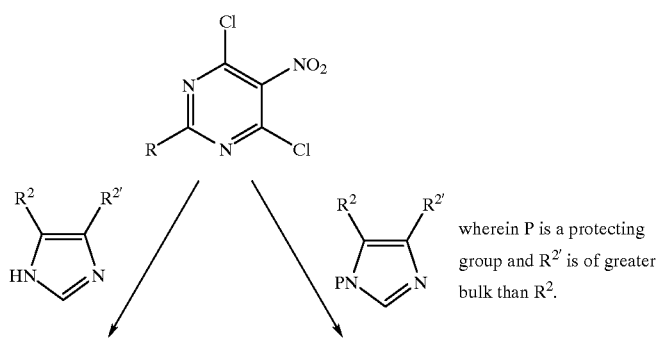
wherein P is a protecting group and $R^{2'}$ is of greater bulk than $R^2$.

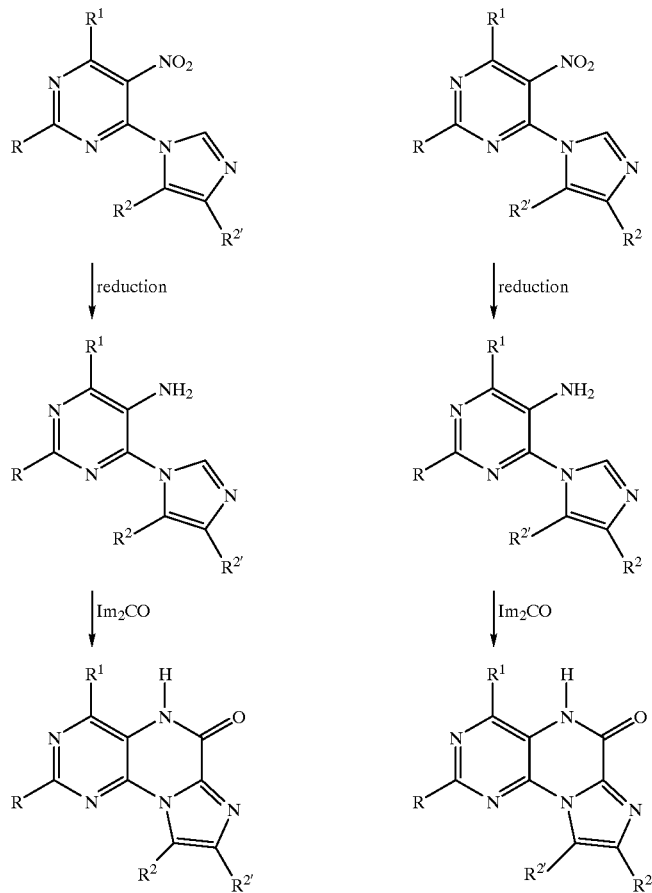

As illustrated in the foregoing Schemes A, A/2, B and C wherein R, $R^1$, A, B and D are as previously defined, an appropriately substituted, chloro or dichloro 5-nitropyrimidine (prepared by methods known in the art) is treated with substituted or non-substituted imidazole, pyrrole, pyrrazole or 1,2,4-triazole (either as their sodium, lithium or potassium salts or with a tertiary amine base) in an aprotic solvent such as acetonitrile, dimethylformamide, dimethyl sulfoxide or methylene chloride, at a temperature of from about −70° C. to about 100° C., to yield either the mono- or di-substituted 5-nitropyrimidine. The nitro group is reduced to the amino group most generally with tin (II) chloride.

In the case of 4- and 4,5-substituted imidazoles, attack by the less hindered nitrogen of the imidazole leads to the major product. Attack by the more hindered nitrogen can be achieved by protecting the less hindered nitrogen with a trityl or a silyl group prior to the displacement reaction. The by-product of this reaction is trityl or silyl halide.

The cyclization procedures known in the art are not sufficient to prepare the compounds of the invention. As for example, the cyclization techniques as utilized in U.S. Pat. No. 4,440,929 would not allow D if formula (I) to be nitrogen, but more importantly when D in formula (I) is $C(R^3)$, $R^3$ could not be loweralkyl, aryl or loweraryloxy, and $R^2$ could only be hydrogen.

The novel cyclization process of this invention is reacting a compound of the following formula (II):

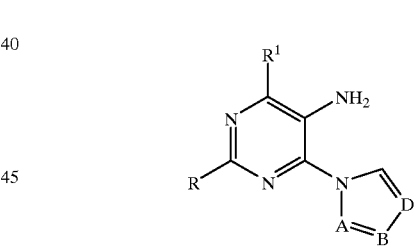

(II)

wherein R, $R^1$, A, B and D have the same meaning as in formula (I), with a one to four equivalent excess of a doubly activated carbonic acid derivative in an inert solvent at a temperature of from about 150° C. to about 200° C. for about 30 minutes to about 6 hours.

The doubly activated carbonic acid derivative is selected from carbonyldiimidazole, diphenyl carbonate, phosgene or an equivalent, preferably carbonyldiimidazole. The aprotic solvent is selected from N-methylpyrollidinone, tetralin, decalin, 1,2-dichlorobenzene, 1,3-dimethyl-2-imidazolidinone, preferably 1,2-dichlorobenzene. The temperature of the reaction is preferably 150–180° C. with a reaction duration of about 1 hour.

After the reaction is completed the reaction mixture is cooled and the final products extracted with aqueous acid or base dependent on the substituents present. The final products are further purified by crystallization or column chromatography.

Method of Use and Pharmaceutical Composition Aspect

The compounds of this invention have been found to generally exhibit cardiovascular effects. More especially they have been found to be combined inotropic and vasodilator agents and to be selective vasodilator agents. Furthermore, among the selective vasodilators they are distinguishable as mixed (arterial and venous) vasodilators, selective venodilators, and selective coronary artery dilators. The combined inotropic vasodilators would be useful in the treatment of congestive heart failure. Likewise, the selective vasodilators with a mixed profile for reduction of preload and afterload on the heart have utility in congestive heart failure; in addition, such agents have utility in the treatment of angina pectoris, hypertension and other disorders of the circulation. Selective venodilators, which decrease the preload on the heart have utility in the treatment of angina pectoris and congestive heart failure. Selective coronary dilators have utility in certain forms of angina pectoris and other coronary vessel related diseases.

The following procedure was used for the initial identification of compounds having vasodilator activity. Such compounds would be useful for the treatment of hypertension or heart failure. The compounds were evaluated by assessing vasodilator activity in rings of canine coronary artery and mesenteric vein in vitro.

Dogs of either sex were anesthetized with pentobarbital (35 mg/kg, i.v.). The heart and mesentery were removed and placed in oxygenated (95% $O_2$/5% $CO_2$) physiological salt solution (PSS) at 37° C. The circumflex coronary artery and the mesenteric vein were dissected free from the adventitia, cut into segments of approximately 2 mm in length, mounted on muscle holders, and placed into 20 mL organ baths filled with PSS, with oxygenation and temperature maintained as above for study under isometric conditions. Optimum preload for each ring was determined with 20 mM KCl followed by a 30 minute relaxation period.

Tissues were checked for endothelial competence by contracting the rings with 20 mM KCl (arteries) or 2 $\mu$M phenylephrine (veins) and then challenging with 1 $\mu$M acetylcholine or 20 U thrombin, respectively. A relaxation of at least 65% was considered acceptable. The vessels were then washed free of drugs and allowed to relax for 30 minutes.

For compound testing, the coronary artery rings were contracted with 50 nM 9,11-dideoxy-11$\alpha$,9$\alpha$-epoxymethano-prostaglandin F$\alpha$ (U46619), and the mesenteric veins were contracted with 2 $\mu$M phenylephrine. These concentrations were chosen to provide approximately 50% of the maximum contraction attainable. Test compounds were added beginning 5 minutes after the contractions had reached a plateau. Additions were made cumulatively as log doses over the concentration range of 10 nM to 100 $\mu$M. Successive doses were added to the bath at 10 minutes intervals or when the previous response had reached a plateau.

After the last dose of test agent, the tissues were washed repeatedly every 10 minutes until complete relaxation was obtained. Tissue viability and endothelium competence was then verified by recontracting the vessels with the prostaglandin (arteries) or phenylephrine (veins) and challenging with acetylcholine or thrombin, respectively, as above.

The compounds which exhibited mixed (arterial and venous) vasodilator activity were then tested for their guanosine 3'-5'-cyclic monophosphate phosphodiesterase inhibition (cGMP-PDEI) characteristics. The mode of testing was a modification of the procedure by W. J. Thompson et al. Those mixed vasodilators with cGMP-PDEI mechanisms should be useful in the treatment of various cardiovascular diseases.

The compounds were tested for their inotropic activity, that is for usefulness as cardiotonic agents, in the ferret papillary muscle contractility model which model is published in *J. Med. Chem.* (1987), Vol. 30, p 1347. The compounds of this invention were substantially free of inotropic activity.

Total effective vascular compliance was measured in pentobarbital-anesthetized dogs pretreated with atropine, propranol, and hexamethonium to block reflex responses and using a sustained infusion of norepinephrine to increase central venous pressure to approximately 5 mm Hg. Animals were instrumented for measurement of left ventricular pressure, aortic pressure, and central venous pressure. Measured volumes of blood were infused and withdrawn and changes in central venous pressure were monitored (see Stewart, D. J., Elsner, D., Sommer, O., Hotz, J. and Bassenge, E., *Circulation* (1986), Vol. 74, pp. 573–582).

Total effective vascular compliance was expressed as the reciprocal of the slope of the volume-pressure curve. This model measures the compliance of the total vascular bed, but, since 85% of the total compliance lies on the venous side, experimental results largely reflect actions on the venous side.

The compounds of the invention which exhibit mixed vasodilator effects and are also cGMP, PDE inhibitors are exemplified by compounds such as 4,9-diethyl-2-(2-ethyl-4-methyl-1H-imidazol-1-yl)-7-methylimidazo[5,1-h]pteridin-6(5H)-one and 9-ethyl-2-(2-ethyl-4-methyl-1H-imidazol-1-yl)-7-methyl-4-(2-propyl)imidazo[5,1-h]pteridin-6(5H)-one.

The compounds of the invention which exhibit mixed vasodilator effects but which are not cGMP-PDE inhibitors are exemplified by compounds such as 9-ethyl-4-[(2-(diethylamino)ethyl)amino]-7-methylimidazo[5,1-h]pteridin-6(5H)-one and 9-ethyl-7-methyl-4-[(2-(morpholin-4-yl)ethyl)amino]imidazo[5,1-h]pteridin-6(5H)-one.

Compounds which exhibit selective venodilator and no cGMP-PDE inhibition are exemplified by 9-ethyl-4-[(1-methylpiperidin-4-yl)amino]-8-phenylimidazo[2,1-h]pteridin-6(5H)-one and compounds which exhibit selective coronary artery dilation and no cGMP-PDE inhibition are exemplified by 4-[(3-(morpholin-4-yl)propyl)amino]-8-phenylimidazo[5,1-h]pteridin-6(5H)-one.

Because the compounds exhibit general cardiovascular activity with specific effects, it is envisioned that they would also prove useful in disease states where bronchodilators, anti-allergies, or topical agents for baldness are indicated.

The compounds of the invention can be administered orally or parenterally. The dosage and method of administration will be dependent on the age, weight, sex and other characteristics of the subject to be treated and the disease state or states to be treated. The compounds when administered orally or parenterally will be admixed with non-toxic pharmaceutically acceptable carriers, which may be solid or liquid in nature, in accordance with standard pharmaceutical practices taking into account the compound/s to be administered, the dosage form and disease state/s to be effected.

Preparations of the compounds include such solid form as powders, tablets, dispersible granules, capsules, cachets and suppositories. Liquid form preparations include solution, suspensions and emulsions. Formulations for topical application would include such forms as creams, aerosols, sprays, powders, lotions, ointments and appliques.

The invention described hereinabove is illustrated below in the Examples which, however, are not to be construed as limiting the invention.

General Procedure for the Preparation of Compounds of Schemes A and A/2

Example 1

2-(1H-imidazol-1-yl)-4-(2-propyl)imidazo[2,1-h]pteridin-6(5H)-one

Combine 29.0 g (0.12 mol) of 2,4-dichloro-5-nitro-6-(2-propyl)pyrimidine with 42.0 g (0.62 mol) of imidazole in 500 mL of acetonitrile, and stir at room temperature for 24 hours. Remove the solvent under vacuum, slurry the residue in 500 mL of $CH_2Cl_2$ and wash with 4×500 mL 10% $K_2CO_3$. Dry the organic portion over $MgSO_4$, treat with charcoal, filter and concentrate the filtrate to dryness under vacuum to afford 2,4-bis(1H-imidazol-1-yl)-5-nitro-6-(2-propyl) pyrimidine.

Dissolve 2,4-bis(1H-imidazol-1-yl)-5-nitro-6-(2-propyl) pyrimidine (16 g, 53.5 mmol) in 300 mL of ethanol and add 35 g of tin (II) chloride dihydrate. Stir for 2 hours at ambient temperature. Remove the solvent under vacuum and slurry the residue in 2 L of $CH_2Cl_2$. Wash with 2×3 L 10% KOH. Dry the $CH_2Cl_2$ portion over $MgSO_4$, treat with charcoal, filter, and concentrate the filtrate under vacuum. Crystallize the residue from ethyl acetate to provide 2,4-bis(1H-imidazol-1-yl)-6-(2-propyl)pyrimidin-5-amine.

Combine 2,4-bis(1H-imidazol-1-yl)-6-(2-propyl) pyrimidin-5-amine (6 g, 22.3 mmol) with 4.5 g (27.8 mmol) of carbonyldiimidazole in 150 mL of 1,2-dichlorobenzene and heat at reflux under $N_2$ for 2 hours. Cool to ambient temperature. Filter the precipitate and wash with $CH_2Cl_2$. Dissolve the solids in 500 mL of 10% HCl, treat with charcoal, filter, and make the filtrate basic with $NH_4OH$. Filter the resulting precipitate, wash with water and then with acetone to provide 2-(1H-imidazol-1-yl)-4-(2-propyl) imidazo[2,1-h]pteridin-6(5H)-one; NMR (DMSO+ $CF_3CO_2D$): δ1.32 (d, 6), 3.84 (m, 1), 7.15 (s, 1), 7.67 (s, 1), 8.04 (s, 1), 8.5 (s, 1) and 8.69 (s, 1 ) ppm.

The following Examples were prepared in a fashion similar to Example 1:

Example 2

9-Ethyl-2-(2-ethyl-4-methyl-1H-imidazol-1-yl)-4,7-dimethylimidazo[5,1-h]pteridin-6(5H)-one Prepared by the treatment of 2,4-dichloro-6-methyl-5-nitropyrimidine with excess 2-ethyl-4-methylimidazole followed by reduction with tin (II) chloride and cyclization with carbonyldiimidazole in refluxing dichlorobenzene.

Example 3

4,9-Diethyl-2-(2-ethyl-4-methyl-1H-imidazol-1-yl)-7-methylimidazo[5,1-h]pteridin-6(5H)-one Prepared by the treatment of 2,4-dichloro-6-ethyl-5-nitropyrimidine with excess 2-ethyl-4-methylimidazole then reduction with tin (II) chloride and cyclization with carbonyidiimidazole in refluxing dichlorobenzene.

Example 4

9-Ethyl-2-(2-ethyl-4-methyl-1H-imidazol-1-yl)-7-methyl-4-(2-propyl)imidazo[5,1-h]pteridin-6(5H)-one Prepared by treatment of 2,4-dichloro-5-nitro-6-(2-propyl)pyrimidine, with excess 2-ethyl-4-methylimidazole followed by reduction with tin (II) chloride and cyclization with carbonyldiimidazole in refluxing dichlorobenzene.

Example 5

4-Ethyl-2-(1H-imidazol-1-yl)imidazo[2,1-h]pteridin-6(5H)-one

Prepared by treatment of 2,4-dichloro-6-ethyl-5-nitropyrimidine with excess imidazole followed by reduction with tin (II) chloride and cyclization with carbonyldiimidazole in refluxing dichlorobenzene.

Example 6

4,9-Diethyl-2-(2-ethyl-1H-imidazol-1-yl)imidazo[5,1-h]pteridin-6(5H)-one

Prepared by treatment of 2,4-dichloro-6-ethyl-5-nitropyrimidine with excess 2-ethylimidazole followed by reduction with tin (II) chloride and cyclization with carbonyidiimidazole in refluxing dichlorobenzene.

uExample 7

4,9-Diethyl-2-(1H-imidazol-1-yl)imidazo[5,1-h] pteridin-6(5H)-one 4,9-Diethyl-2-(2-ethyl-1H-imidazol-1-yl)imidazo[5,1-h] pteridin-6(5H)-one (5.0 g, 15 mmol) is heated with 50 g of imidazole at 200° C. under $N_2$ for 16 hours. The reaction mixture is cooled to −100° C. and 150 mL of methanol is added. The solids are filtered and washed with methanol to provide 4,9-diethyl-2-(1H-imidazol-1-yl)imidazo[5,1-h] pteridin-6(5H)-one.

Example 8

9-Ethyl-2-(2-ethyl-1H-imidazol-1-yl)-4-propylimidazo[5,1-h]pteridin-6(5)-one

Prepared by treatment of 3,4-dichloro-5-nitro-6-propylpyrimidine with excess 2-ethylimidazole followed by reduction with tin (II) chloride and cyclization with carbonyidiimidazole in refluxing dichlorobenzene.

Example 9

9-Ethyl-2-(1H-imidazol-1-yl)-4-propylimidazo[5,1-h]pteridin-6(5H)-one

Prepared by treatment of 9-ethyl-2-(2-ethyl-1H-imidazol-1-yl)-4-propylimidazo[5,1-h]pteridin-6(5H-one with excess imidazole at 200° C.

Example 9a

4-Ethyl-9-(1-ethylpropyl)-2-(2-(1-ethylpropyl)-1H-imidazol-1-yl)imidazo[5,1-h]pteridin-6(5H)-one Prepared by treatment of 2,4-dichloro-6-ethyl-5-nitropyrimidine with excess 2-(1-ethylpropyl)imidazole followed by reduction with tin (II) chloride and cyclization with carbonyidiimidazole in refluxing dichlorobenzene.

Example 9b

4-Ethyl-9-(1-ethylpropyl)-2-(1H-imidazol-1-yl) imidazo[5,1 -h]pteridin-6(5H)-one Prepared by treatment of the product of Example 9a with excess imidazole at 200° C.

Example 9c

4-Ethyl-9-(2-cyclohexylethyl)-2-(2-(2-cyclohexylethyl)-1H-imidazol-1-yl)imidazo[5,1-h] pteridin-6(5H)-one Prepared by treatment of 2,4-dichloro-6-ethyl-5-nitropyrimidine with excess 2-(2-cyclohexylethyl)imidazole followed by reduction with tin (II) chloride and cyclization with carbonyldiimidazole in refluxing dichlorobenzene.

Example 9d

4-Ethyl-9-(2-cyclohexylethyl)-2-(1H-imidazol-1-yl) imidazo[5,1-h]pteridin-6(5H)-one Prepared by treatment of the product of Example 9c with excess imidazole at 200° C.

Example 9e

4-Ethyl-9-(2-phenylethyl)-2-(2-(2-phenylethyl)-1H-imidazol-1-yl)imidazo[5,1-h]pteridin-6(5H)-one Prepared by treatment of 2,4-dichloro-6-ethyl-5-nitropyrimidine with excess 2-(2-phenylethyl)imidazole followed by reduction with tin (II) chloride and cyclization with carbonyldiimidazole in refluxing dichlorobenzene.

Example 9f 9-(1,5-Dimethyl-4-hexenyl)-2-(2-(1,5-dimethyl-4-hexenyl)-1H-imidazol-1-yl)-4-ethylimidazo[5,1-h]pteridin-6(5H)-one Prepared by treatment of 2,4-dichloro-6-ethyl-5-nitropyrimidine with excess 2-(1,5-dimethyl-4-hexenyl)imidazole followed by reduction with tin (II) chloride and cyclization with carbonyldiimidazole in refluxing dichlorobenzene.

Example 9g 9-(1,5-Dimethyl-4-hexenyl)-2-(1H-imidazol-1-yl)-4-ethylimidazo[5,1-h]pteridin-6(5H)-one Prepared by treatment of the product of Example 9f with excess imidazole at 200° C.

Example 9h 9-(3-Butenyl)-2-(2-(3-butenyl)-1H-imidazol-1-yl)-4-ethylimidazo[5,1-h]pteridin-6(5H)-one Prepared by treatment of 2,4-dichloro-6-ethyl-5-nitropyrimidine with excess 2-(3-butenyl)imidazole followed by reduction with tin (II) chloride and cyclization with carbonyldiimidazole in refluxing dichlorobenzene.

Example 9i 9-(3-Butenyl)-2-(1H-imidazol-1-yl)-4-ethylimidazo[5,1-h]pteridin-6(5H)-one Prepared by treatment of the product of Example 9h with excess imidazole at 200° C.

Example 9j 9-(3,4-Dihydroxybutyl)-4-ethyl-2-(1H-imidazol-1-yl)imidazo[5,1-h]pteridin-6(5H)-one Dissolve 5.25 g (15.7 mmol) of the product of Example 9i in 100 mL of acetic acid at 0° C. Add 2.79 g (15.7 mmol) of N-bromosuccinimide and 2.61 g (15.6 mmol) of silver acetate, and stir the mixture at ambient temperature for 24 hours. Add 500 mL of 9/1 acetic acid/water and heat to 90° C. for 16 hours. Filter the mixture through Celite, evaporate the solvent, and dissolve the residue in 1 N HCl. Treat the solution with charcoal, filter, and make basic with concentrated NH$_4$OH. Collect the precipitate and wash with water and acetonitrile. Suspend the precipitate in 200 mL of 3/1 methanol/concentrated NH$_4$OH and heat to reflux for 8 hours. Evaporate the mixture, dissolve the residue in 2N HCl, and precipitate with concentrated NH$_4$OH. Collect the precipitate and wash with water and acetonitrile. Triturate the precipitate with boiling methanol, DMF and then again with methanol to provide the title compound.

Example 10

2-(2-(1H-Imidazol-1-yl)methyl-1H-imidazol-1-yl)-9-((1H-imidazol-1-yl)methyl-4-(2-propyl)imidazo[5,1-h]pteridin-6(5H)-one Prepared by treatment of 2,4-dichloro-5-nitro-6-(2-propyl)pyrimidine with 2.1 eq. of the sodium salt of 2-(1H-imidazol-1-yl)methyl imidazole followed by reduction with tin (II) chloride, and cyclization with carbonyidiimidazole in refluxing dichlorobenzene.

Example 11

2-(1H-Imidazol-1-yl)-9-((1H-imidazol-1-yl)methyl-4-(2-propyl)imidazo-[5,1-h]pteridin-6(5H)-one Prepared by treatment of the product of Example 10 with excess imidazole at 200° C.

Example 12

4-Ethyl-2-(1,2,4-triazol-1-yl)triazolo[5,1-h]pteridin-6(5H)-one

Prepared by treatment of 2,4-dichloro-6-ethyl-5-nitropyrimidine with excess triazole, followed by reduction with tin (II) chloride and cyclization with carbonyldiimidazole.

Example 13

4-(2-Butyl)-2-(pyrrazol-1-yl)pyrrazolo[5,1-h]pteridin-6(5H)-one

Prepared by treatment of 2,4-dichloro-6-(2-butyl)-5-nitropyrimidine with excess pyrrazole, followed by reduction with tin (II) chloride and cyclization with carbonyldiimidazole.

Example 14

4-Cyclopentyl-9-ethyl-2-(2-ethylpyrrol-1-yl)pyrrolo[2,1-h]pteridin-6(5)-one

Prepared by treatment of 2,4-dichloro-6-cyclopentyl-5-nitropyrimidine with 2 eq. of sodium pyrrole followed by reduction with tin (II) chloride and cyclization with carbonyidiimidazole.

Example 14a 8,9-dimethyl-2-(4,5-dimethyl-1H-imidazol-1-yl)imidazo[2,1-h]pteridin-6(5H)-one Prepared by reaction of excess 4,5-dimethylimidazole with 2,4-dichloro-5-nitropyrimidine followed by reduction with tin (II) chloride and cyclization with carbonyldiimidazole.

General Procedure for the Preparation of Compounds of Scheme B

Example 15

4-(Dimethylamino)-9-((morpholin-4-yl)methyl)imidazo[5,1-h]pteridin-6(5H)-one

Dissolve 50 g (0.26 mol) of 4,6-dichloro-5-nitropyrimidine in 500 mL of CH$_2$Cl$_2$ and cool to −70° C. Add a solution of 24 mL (0.28 mol) dimethylamine, 70 mL (0.40 mol) of diisopropylethylamine, and 100 mL of CH$_2$Cl$_2$ over 30 minutes. Warm to ambient temperature and wash the reaction mixture with 500 mL of 20% K$_2$CO$_3$. Dry the CH$_2$Cl$_2$ portion over MgSO$_4$, treat with charcoal filter, and remove the filtrate under vacuum. Crystallize the residue with ether to provide 4-dimethylamino-6-chloro-5-nitropyrimidine.

Combine 12 g (59 mmol) of 4-dimethylamino-6-chloro-5-nitropyrimidine with 10 g (60 mmol) of 2-((morpholin-4-yl)methyl)imidazole and 20 mL (0.12 mol) of diisopropylethylamine in 250 mL of acetonitrile and heat at reflux for 24 hours. Remove the solvent under vacuum and dissolve the residue tin 500 mL of methylene chloride. Wash the methylene chloride solution with two 500 mL portions of 10% KOH, dry over MgSO$_4$, treat with charcoal, filter and concentrate under vacuum. Crystallize the residue from ether, NMR (CDCl$_3$) δ2.27 (t, 4), 3.20 (s, 6), 3.42 (t, 4), 3.74 (s, 2), 7.01 (d, 1), 7.11 (d, 1) and 8.50 (s, 1) ppm.

Combine the above crystallized residue (9.0 g, 27 mmol) with 25 mL cyclohexane, 2 g of palladium on carbon, and 150 mL of ethanol and reflux for 4 hours. Remove the catalyst by filtration and concentrate the filtrate under vacuum. Crystallize the residue from ether, NMR (CDCl$_3$) δ2.38 (t, 4), 3.01 (s, 6), 3.48 (t, 4), 3.67 (s, 2), 3.77 (s, 2), 7.14 (d, 2), and 8.27 (s, 1) ppm.

Combine 6 g (18 mmol) of the above amino compound with 3.5 g (22 mol) of carbonyldiimidazole in 150 mL of 1,2-dichlorobenzene and heat at reflux under N$_2$ for 2 hours. Cool to ambient temperature and chromatograph on 300 g of silica get using 2% MeOH/CH$_2$Cl$_2$. Combine the appropriate fractions and concentrate under vacuum. Crystallize the residue from ethyl acetate to provide 4-(dimethylamino)-9-((morpholin-4-yl)methyl)imidazo[5,1-h]pteridin-6(5h)-one, NMR (DMSO): δ2.60 (t, 4), 3.03 (s, 6), 3.52 (t, 4), 4.37 (s, 2), 7.85 (s, 1), 8.39 (s, 1), and 10.65 (s, 1) ppm.

The following compounds were prepared in a fashion similar to Example 15:

Example 16

9-Ethyl-4-[(2-(pyridin-2-yl)ethyl)methylamino]imidazo[5,1-h]pteridin-6(5H)-one

Prepared by treatment of 4,6-dichloro-5-nitropyrimidine with 2-(2-(methylamino)ethyl)pyridine followed by reaction with 2-ethylimidazole, reduction with tin (II) chloride and cyclization with carbonyidiimidazole.

Example 17

9-Ethyl-4-[(1-methylpiperidin-4-yl)methylamino]imidazo[5,1 -h]pteridin-6(5H)-one Prepared by treatment of 4,6-dichloro-5-nitropyrimidine with 1-methyl-4-(methylamino)piperidine followed by reaction with 2-ethylimidazole, reduction with palladium on carbon and cyclohexene in refluxing ethanol, and cyclization with carbonyidiimidazole.

Example 18

4-[(1-Methylpiperidin-4-yl)methylamino]-8-phenylimidazo[2,1-h]pteridin-6(5H)-one Prepared by treatment of 6-chloro-N-methyl-N-(1-methylpiperidin-4-yl)-5-nitropyrimidin-4-amine with 4-phenylimidazole followed by reduction with tin (II) chloride and cyclization with carbonyidiimidazole.

Example 19

9-Ethyl-4-[(phenylmethyl)methylamino]imidazo[5,1-h]pteridin-6(5H)-one

Prepared by treatment of 4,6-dichloro-5-nitropyrimidine with N-methyl benzylamine, reaction with 2-ethylimidazole, reduction with tin (II) chloride and cyclization with carbonyldiimidazole.

Example 20

9-Ethyl-4-(methylamino)imidazo[5,1-h]pteridin-6(5H)-one

Prepared by hydrogenation of the product of Example 19 with palladium on carbon in ethanol containing 2 eq. NaOH, at 50 psi and 50° C. for 24 hours. The catalyst was removed and the product was precipitated by addition of a saturated solution of ammonium chloride. The solids were filtered and washed with water and ethanol to provide 9-ethyl-4-(methylamino)imidazo[5,1-h]pteridin-6(5H)-one.

Example 21

9-Ethyl-7-methyl-4-[((2-dimethylamino)ethyl)methylamino]-imidazo[5,1 -h]pteridin-6(5H)-one Prepared by treatment of 4,6-dichloro-5-nitropyrimidine with N,N,N'-trimethylethylenediamine followed by reaction with 2-ethyl-4-methylimidazole, reduction with tin (II) chloride and cyclization with carbonyldiimidazole.

Example 22

9-Ethyl-4-[((2-dimethylamino)ethyl)methylamino]imidazo[5,1-h]pteridin-6(5H)-one

Prepared by treatment of 4,6-dichloro-5-nitropyrimidine with N,N,N'-trimethylethylenediamine followed by reaction with 2-ethylimidazole, reduction with tin (II) chloride and cyclization with carbonyldiimidazole.

Example 23

9-Ethyl-4-[(1-methylpiperidin-4-yl)amino]imidazo[5,1-h]pteridin-6(5H)-one

Prepared by treatment of 4,6-dichloro-5-nitropyrimidine with 1-methyl-4-(benzylamino)piperidine, followed by reaction with 2-ethylimidazole, reduction with tin (II) chloride, cyclization with carbonyldiimidazole and debenzylation with refluxing 6 N HCl for 30 minutes.

Example 23a 4-((2-(Diethylamino)cyclohexyl)amino)-9-ethylimidazo[5,1 -h]pteridin-6(5H)-one Prepared by treatment of 4,6-dichloro-5-nitropyrimidine with N-benzyl-2-(diethylamino)cyclohexylamine, followed by reaction with 2-ethylimidazole, reduction with tin (II) chloride, cyclization with carbonyldiimidazole and debenzylation with refluxing 5 N HCl for 3 hours.

Example 24

9-Ethyl-4-[(2-(phenylmethoxy)ethyl)methylamino]imidazo[5,1-h]pteridin-6(5H)-one

Prepared by treatment of N-(2-(phenylmethoxy)ethyl)methylamine with 4,6-dichloro-5-nitropyrimidine, followed by reaction with 2-ethylimidazole, reduction with tin (II) chloride and cyclization with carbonyldiimidazole.

Example 25

9-Ethyl-4-[(2-hydroxyethyl)methylamino]imidazo[5,1-h]pteridin-6(5H)-one

Prepared by hydrogenation of the product of Example 24 with palladium on carbon in methanol containing 1.1 eq. NaOH at 50 psi for 8 hours.

Example 26

9-Ethyl-4-[(2-hydroxyethyl)methylamino]imidazo[5,1-h]pteridin-6(5H)-one

Prepared by treatment of 4,6-dichloro-5-nitropyrimidine with N-(2-(benzyloxy)ethylbenzylamine, followed by reaction with 2-ethyl-4-methylimidazole, reduction with tin (II) chloride, cyclization with carbonyldiimidazole, and hydrogenation with palladium on carbon in methanol containing 1.1 eq. NaOH at 50 psi and 500 for 24 hours.

Example 27

9-Ethyl-7-methyl-4-(dimethylamino)imidazo[5,1-h] pteridin-6(5H)-one

Prepared by treatment of 4,6-dichloro-5-nitropyrimidine with dimethylamine, followed by reaction with 2-ethyl-4-methylimidazole, reduction with tin (II) chloride, and cyclization with carbonyidiimidazole.

Example 28

9-Ethyl-7-methyl-4-(dimethylamino)-2-(methylthio) imidazo[5,1-h]pteridin-6(5H)-one Prepared by treatment of 4,6-dichloro-5-nitro-2-(methylthio)pyrimidine with dimethylamine, followed by reaction with 2-ethyl-4-methylimidazole, reduction with tin (II) chloride, and cyclization with carbonyidiimidazole.

Example 29

9-Ethyl-7-methyl-4-(dimethylamino)-2-(methylsulfonyl)imidazo[5,1-h]pteridin-6(5H)-one Prepared by oxidation of the product of Example 28 with 3 eq. of meta-chloroperbenzoic acid at 0–20° C. in 10% methanol/methylene chloride. The reaction mixture is washed twice with 5% KHCO$_3$. The organic portion is dried over MgSO$_4$, charcoal treated, and concentrated to near dryness. The residue is crystallized with acetonitrile to provide the title compound.

Example 30

9-Ethyl-4-[N-(phenylmethyl)methylamino]-2-methylthio)imidazo[5,1-h]pteridin-6(5H)-one Prepared by treatment of 4,6-dichloro-5-nitro-2-(methylthio)pyrimidine with N-benzyl methylamine, followed by reaction with 2-ethylimidazole, reduction with tin (II) chloride, and cyclization with carbonyldiimidazole.

Example 31

9-Ethyl-4-[N-(phenylmethyl)methylamino]-2-(methylsulfonyl)imidazo[5,1-h]pteridin-6(5H)-one Prepared by the oxidation of the product of Example 30 with 3 eq. of meta-chloroperbenzoic acid in 10% methanol/methylene chloride at 0–20° C.

Example 32

9-Ethyl-2-[((2-diethylamino)ethyl)amino]-4-[N-(phenylmethyl)methylamino]imidazo[5,1-h]pteridin-6(5H)-one Prepared by the treatment of the product of Example 31 with 10 eq. of N,N-diethylethylenediamine at 120° C. for 4 hours. The excess diamine was removed under vacuum and the residue precipitated with 10% K$_2$CO$_3$. The solids were filtered, washed with water, then acetone, to provide the title compound.

Example 33

9-Ethyl-2-[((2-diethylamino)ethyl)amino]-4-(methylamino)imidazo[5,1-h]pteridin-6(5H)-one Prepared from the product of Example 32 by hydrogenation with palladium on carbon in methanol with 1 eq. NaOH at 50° C. and 50 psi for 24 hours.

Example 34

9-Ethyl-4-[((2-diethylamino)ethyl)amino]-7-methylimidazo[5,1-h]pteridin-6(5H)-one Prepared by treatment of 4,6-dichloro-5-nitropyrimidine with N,N-diethyl-N-benzylethylene diamine, followed by reaction with 2-ethyl-4-methylimidazole, reduction with tin (II) chloride, cyclization with carbonyldiimidazole and debenzylation with 6 N HCl.

Example 35

9-Ethyl-7-methyl-4-[2-(morpholin-4-yl)ethyl) amino]imidazo[5,1-h]pteridin-6(5H)-one Prepared by treatment of 4,6-dichloro-5-nitropyrimidine with 4-(2-benzylamino)ethylmorpholine, followed by reaction with 2-ethyl-4-methylimidazole, reduction with tin (II) chloride, cyclization with carbonyldiimidazole and debenzylation with 6 N HCl.

Example 36

9-Ethyl-7-methyl-4-[(3-(morpholin-4-yl)propyl) amino]imidazo[5,1-h]pteridin-6(5H)-one Prepared by treatment of 4,6-dichloro-5-nitropyrimidine with 4-(2-benzylamino)ethylmorpholine, followed by reaction with 4-phenylimidazole, reduction with tin (II) chloride, cyclization with carbonyldiimidazole and debenzylation with 6 N HCl.

Example 37

4-[(2-(Morpholin-4-yl)ethyl)amino]-8-phenylimidazo[2,1-h]pteridin-6(5H)-one

Prepared by treatment of 4,6-dichloro-5-nitropyrimidine with 4-(2-benzylamino)ethylmorpholine, followed by reaction with 4-phenylimidazole, reduction with tin (II) chloride, cyclization with carbonyldiimidazole and debenzylation with 6 N HCl.

Example 38

4-[(3-(Morpholin-4-yl)propyl)amino]-8-phenylimidazo[2,1-h]pteridin-6(5H)-one

Prepared by treatment of 4,6-dichloro-5-nitropyrimidine with 4-(3-benzylamino)propylmorpholine, followed by reaction with 4-phenylimidazole, reduction with tin (II) chloride, cyclization with carbonyldiimidazole and debenzylation with 6 N HCl.

Example 39

9-(1H-imidazol-1-yl)methyl-4-[(2-(morpholin-4-yl) ethyl)amino]-imidazo[5,1-h]pteridin-6(5H)-one Prepared by treatment of 4,6-dichloro-5-nitropyrimidine with 4-(2-benzylamino)ethylmorpholine, followed by reaction with 2-((1H-imidazol-1-yl)methyl)imidazole, reduction with tin (II) chloride, cyclization with carbonyldiimidazole and hydrogenation with palladium on carbon in ethanol containing 1.1 eq. NaOH at 50° C. and 50 psi.

Example 40

9-Ethyl-4,7-dimethyl-2-(methylthio)imidazo[5,1-h] pteridin-6(5H)-one

Prepared by treatment of 4-chloro-6-methyl-2-(methylthio)-5-nitropyrimidine with 2-ethyl-4- methylimidazole, reduction with tin (II) chloride, and cyclization with carbonyidiimidazole.

Example 41

9-Ethyl-4,7-dimethyl-2-(methylsulfonyl)imidazo[5,1-h]pteridin-6(5H)-one

Prepared by the oxidation of the product of Example 40 with 3.0 eq. of meta-chloroperbenzoic acid in 20% methanol/methylene chloride at 0° C.

Example 41a

4,9-Diethyl-7-methyl-2-(methylthio)imidazo[5,1-h]pteridin-6(5H)-one

Prepared by treatment of 4-chloro-6-methyl-2-(methylthio)-5-nitropyrimidine with 2-ethyl-4-methylimidazole, reduction with tin (II) chloride, and cyclization with carbonyidiimidazole.

Example 41b

4,9-Diethyl-7-methyl-2-(methylsulfonyl)imidazo[5,1-h]pteridin-6(5H)-one

Prepared by the oxidation of the product of Example 41a with 4.0 eq. of meta-chloroperbenzoic acid in 5% methanol/methylene chloride at 0° C.

Example 41c

2-((2,3-Dihydroxypropyl)amino)-4,9-Diethyl-7-methylimidazo[5,1-h]pteridin-6(5H)-one

Prepared by the treatment of the product of Example 41b with 10 eq. of 3-amino-1,2-propanediol in N-methylpyrrolidinone at 100° C. for 18 hours. The mixture was poured on water to precipitate the product. The solids were filtered, washed with water, and then acetonitrile, to provide the title compound.

Example 42

9-(1H-imidazol-1-yl)methyl-4-[(2-phenylethyl)amino]imidazo[5,1-h]pteridin-6(5H)-one

Prepared by treatment of 4,6-dichloro-5-nitropyrimidine with N-benzylphenethylamine, followed by reaction with 2-((1H-imidazol-1-yl)methyl)imidazole, reduction with tin (II) chloride, cyclization with carbonyidiimidazole and hydrogenation with palladium on carbon in ethanol containing 1.1 eq. NaOH at 50° C. and 50 psi.

Example 43

8-Ethyl-4-[(2-(diethylamino)ethyl)amino]imidazo[2,1-h]pteridin-6(5H)-one

Prepared by reaction of 4,6-dichloro-5-nitropyrimidine with N,N-diethyl-N'-benzylethylenediamine, followed by displacement with 4-ethylimidazole, reduction with tin (II) chloride, cyclization with carbonyidiimidazole and debenzylation with 6 N HCl.

Example 44

9-Ethyl-4-[(2-(diethylamino)ethyl)amino]imidazo[2,1-h]pteridin-6(5H)-one

Prepared by reaction of 4,6-dichloro-5-nitropyrimidine with N,N-diethyl-N'-benzylethylenediamine, followed by displacement with 1-trityl-4-ethylimidazole, reduction with tin (II) chloride, cyclization with carbonyidiimidazole and deprotection with 6 N HCl.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (I):

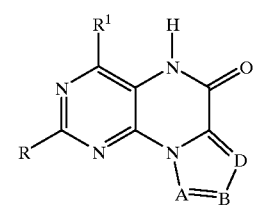

wherein

A is N or $C(R^2)$;

B is N or $C(R^2)$;

D is N or $C(R^3)$;

R is hydrogen, hydroxy, loweralkyl, loweralkoxy, cycloalkyl, aryl, aryloxy, pyridinyl, 3-pyridinyloxy, $R^6S(O)_n$, W—ALK—Q, or —$N(R^7)_2$;

or R is

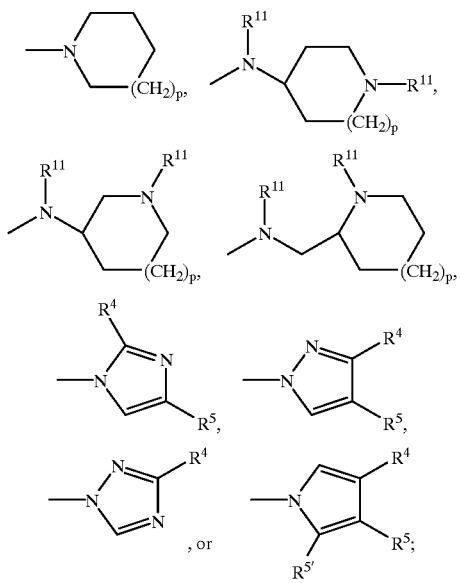

$R^1$ is hydrogen, hydroxy, loweralkyl, loweralkoxy, cycloalkyl, aryl, aryloxy, pyridinyl, 3-pyridinyloxy, $R^6S(O)_n$, W—ALK—Q, or —$N(R^7)_2$, or $R^1$ is

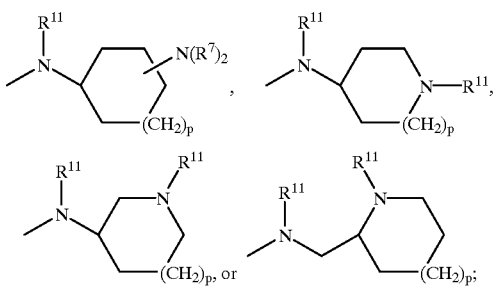

$R^2$ is hydrogen, $C_1$–$C_8$ straight or branched chain alkyl optionally substituted by 2 adjacent hydroxyl groups, $C_3$–$C_8$ straight or branched chain alkenyl, loweralkylloweralkoxy, aryl, pyridinyl, loweralkylcycloalkyl, loweralkylaryl, loweralkylpyridinyl, loweralkylaryloxy, loweralkylpyridinyloxy, loweralkyl-$N(R^6)_2$, or

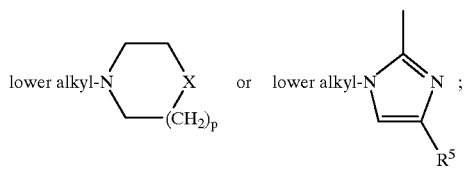

$R^3$ is hydrogen, loweralkyl, aryl, pyridinyl, loweralkylaryloxy, or loweralkylpyridinyl;
$R^4$ is hydrogen, $C_1$–$C_8$ straight or branched chain alkyl, $C_3$–$C_8$ straight or branched chain alkenyl, loweralkylcycloalkyl or loweralkylaryl;
$R^5$ and $R^{5'}$ are the same or independently hydrogen or loweralkyl;
$R^6$ is loweralkyl, aryl, pyridinyl, loweralkylaryl or loweralkylpyridinyl; each $R^7$ is the same or independently hydrogen, loweralkyl, aryl or pyridinyl;
$R^8$ is the same as $R^7$;
Q is —O—, —$N(R^9)$—, —S—, —$CH_2O$—, —$CH_2N(R^9)$— or —$CH_2S$—;
W is hydrogen, hydroxy, loweralkyl, loweralkoxy, aryl, aryloxy, pyridinyl which may be substituted by one or two hydroxy groups, pyridinyloxy, —$N(R^{10})_2$, or

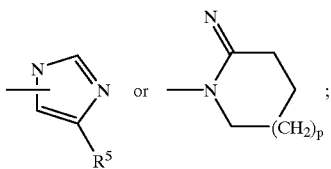

$R^9$ and $R^{10}$ have the same meaning as $R^7$;
$R^{11}$ are the same or independently hydrogen or methyl;
X is —$CH_2$—, —O—, —$S(O)_n$—, —$NR^{10}$—;
ALK is a $C_1$–$C_4$ straight or branched chain alkyl optionally substituted by a mono hydroxyl group which cannot be attached to the carbon atom adjacent to Q or W when Q or W are heteroatoms, and
n is 0, 1 or 2; and
p is 0 or 1, or a pharmaceutically acceptable salt thereof, with the provisos that (a) only one of A and B is N; and (b) only one of B and D is N.

2. A compound of claim 1 wherein A is N, B is $C(R^2)$ and D is $C(R^3)$.
3. A compound of claim 1 wherein A is N, B is $C(R^2)$ and D is N.
4. A compound of claim 1 wherein A is $C(R^2)$, B is N and D is $C(R^3)$.
5. A compound of claim 1 wherein A is $C(R^2)$, B is $C(R^2)$ and D is N.
6. A compound of claim 1 selected from the group consisting of the following compounds:
4-ethyl-9-(1-ethylpropyl)-2-(2-(1-ethylpropyl)-1H-imidazol-1-yl)imidazo[5,1-h]pteridin-6(5H)-one;
4-ethyl-9-(1-ethylpropyl)-2-(1H-imidazol-1-yl)imidazo[5,1-h]pteridin-6(5H)-one;
4-ethyl-9-(2-cyclohexylethyl)-2-(2-(2-cyclohexylethyl)-1H-imidazol-1-yl)imidazo[5,1-h]pteridin-6(5H)-one;
4-ethyl-9-(2-cyclohexylethyl)-2-(1H-imidazol-1-yl)imidazo[5,1-h]pteridin-6(5H)-one;
4-ethyl-9-(2-phenylethyl)-2-(2-(2-phenylethyl)-1H-imidazol-1-yl)imidazo[5,1-h]pteridin-6(5H)-one;
9-(1,5-dimethyl-4-hexenyl)-2-(2-(1,5-dimethyl-4-hexenyl)-1H-imidazol-1-yl)-4-ethylimidazo[5,1-h]pteridin-6(5H)-one;
9-(1,5-dimethyl-4-hexenyl)-2-(1H-imidazol-1-yl)-4-ethylimidazo[5,1-h]pteridin-6(5H)-one;
9-(3-butenyl)-2-(2-(3-butenyl)-1H-imidazol-1-yl)-4-ethylimidazo[5,1-h]pteridin-6(5H)-one;
9-(3-butenyl)-2-(1H-imidazol-1-yl)-4-ethylimidazo[5,1-h]pteridin-6(5H)-one;
9-(3,4-dihydroxybutyl)-4-ethyl-2-(1H-imidazol-1-yl)imidazo[5,1-h]pteridin-6(5H)-one;
2-(2-(1H-imidazol-1-yl)methyl-1H-imidazol-1-yl)-9-((1H-imidazol-1-yl)methyl-4-(2-propyl)imidazo[5,1-h]pteridin-6(5H)-one;
2-(1H-imidazol-1-yl)-9-((1H-imidazol-1-yl)methyl-4-(2-propyl)imidazo[5,1-h]pteridin-6(5H)-one;
4-ethyl-2-(1,2,4-triazol-1-yl)triazolo[5,1-h]pteridin-6(5H)-one;
4-(2-butyl)-2-(pyrrazol-1-yl)pyrrazolo[5,1-h]pteridin-6(5H)-one;
4-cyclopentyl-9-ethyl-2-(2-ethylpyrrol-1-yl)pyrrolo[2,1-h]pteridin-6(5H)-one;
8,9-dimethyl-2-(4,5-dimethyl-1H-imidazol-1-yl)imidazo[2,1-h]pteridin-6(5H)-one;
9-ethyl-7-methyl-4-[((2-dimethylamino)ethyl)methylamino]imidazo[5,1-h]pteridin-6(5H)-one;
9-ethyl-4-[((2-dimethylamino)ethyl)methylamino]imidazo[5,1-h]pteridin-6(5H)-one;
4-((2-(diethylamino)cyclohexyl)amino)-9-ethylimidazo[5,1-h]pteridin-6(5H)-one;
9-ethyl-4-[(2-(phenylmethoxy)ethyl)methylamino]imidazo[5,1-h]pteridin-6(5H)-one;
9-ethyl-4-[N-(phenylmethyl)methylamino]-2-(methylthio)imidazo[5,1-h]pteridin-6(5H)-one;
9-ethyl-7-methyl-4-[(2-(morpholin-4-yl)ethyl)amino]imidazo[5,1-h]pteridin-6(5H)-one;
9-ethyl-7-methyl-4-[(3-(morpholin-4-yl)propyl)amino]imidazo[5,1-h]pteridin-6(5H)-one;
4-[(2-(morpholin-4-yl)ethyl)amino]-8-phenylimidazo[2,1-h]pteridin-6(5H)-one;
4-[(3-(morpholin-4-yl)propyl)amino]-8-phenylimidazo[2,1-h]pteridin-6(5H)-one;

9-(1H-imidazol-1-yl)methyl-4-[(2-(morpholin-4-yl)ethyl)amino]imidazo[5,1-h]pteridin-6(5H)-one;

9-ethyl-4,7-dimethyl-2-(methylthio)imidazo[5,1-h]pteridin-6(5H)-one;

9-ethyl-7-methyl-4-[((2-dimethylamino)ethyl)methylamino]imidazo[5,1-h]pteridin-6(5H)-one;

4,9-diethyl-7-methyl-2-(methylthio)imidazo[5,1-h]pteridin-6(5H)-one;

4,9-diethyl-7-methyl-2-(methylsulfonyl)imidazo[5,1-h]pteridin-6(5H)-one;

2-((2,3-dihydroxypropyl)amino)-4,9-Diethyl-7-methylimidazo[5,1-h]pteridin-6(5H)-one; and 9-(1H-imidazol-1-yl)methyl-4-[(2-phenylethyl)amino]imidazo[5,1-h]pteridin-6(5H)-one.

* * * * *